United States Patent
Chen (10) Patent No.: US 9,480,591 B2
(45) Date of Patent: Nov. 1, 2016

(54) ADJUSTABLE LIMB PROTECTIVE ASSEMBLY

(71) Applicant: Tung-Cheng Chen, Taichung (TW)

(72) Inventor: Tung-Cheng Chen, Taichung (TW)

( * ) Notice: Subject to any disclaimer, the term of this patent is extended or adjusted under 35 U.S.C. 154(b) by 234 days.

(21) Appl. No.: 14/499,673

(22) Filed: Sep. 29, 2014

(65) Prior Publication Data

US 2016/0089258 A1    Mar. 31, 2016

(51) Int. Cl.
*A61F 5/01* (2006.01)

(52) U.S. Cl.
CPC ................... *A61F 5/0102* (2013.01)

(58) Field of Classification Search
CPC ............ A61G 13/1235; A61F 5/0123; A61F 5/0125; A61F 2005/0139; A61F 5/0102; A61F 2005/0167; A61F 5/0118; A61F 5/05866; A61F 5/10; A61F 13/107; A61F 5/013; A61F 5/3738; A61F 5/3753; A61F 5/3761; A61F 5/05858; A61F 5/3723; A61F 5/37

See application file for complete search history.

*Primary Examiner* — Ophelia A Hawthorne
(74) *Attorney, Agent, or Firm* — Rosenberg, Klein & Lee (57) ABSTRACT

An adjustable limb protective assembly has a main body, a first covering frame and a second covering frame. The main body has a first extending arm, a second extending arm, two holding bases, two operating elements and a jointing connector. Each extending arm has a connecting board. The holding bases are respectively connected to the extending arms adjacent the connecting boards. The operating elements are respectively and securely mounted on the connecting boards, and each one of the operating elements has an operating mount and an operating stem. The jointing connector is connected to the extending arms. The first covering frame is connected to the first extending arm and has a first supporting arm and a first covering base. The second covering frame is connected to the second extending arm and has a second supporting arm and a second covering base.

10 Claims, 9 Drawing Sheets

ADJUSTABLE LIMB PROTECTIVE ASSEMBLY

BACKGROUND OF THE INVENTION

1. Field of the Invention

The present invention relates to a protective assembly, and more particularly to an adjustable limb protective assembly that can be adjusted to fit with different users' limbs conveniently and safely.

2. Description of Related Art

A conventional adjustable limb protective assembly is used to keep the injured limbs of a user at a proper posture to protect the limbs from being injured again. The conventional adjustable limb protective assembly comprises a main body and two covering frames. The main body has two extending arms and a jointing connector. The extending arms are pivotally connected to each other at a pivot point, and each one of the extending arms has a pivot end, a connecting end and an adjusting slot. The pivot ends of the extending arms are pivotally connected to each other. The adjusting slot is elongated and is formed through the extending arm near the connecting end of the extending arm. The jointing connector is mounted at the pivot point between the extending arms, is mounted around the pivot ends of the extending arms, and is used to limit an angle between the extending arms.

The covering frames are respectively connected to the extending arms of the main body, and each one of the covering frames has a connecting base and at least one belt. The connecting base is mounted around the connecting end of a corresponding extending arm and has a connecting hole and a pressing button. The connecting hole is formed through the connecting base and communicates with the adjusting slot of the corresponding extending arm. The pressing button is pressably mounted in the connecting hole of the connecting base and is selectively and securely mounted in the adjusting slot of the corresponding connecting base. The at least one belt is connected to the connecting base and is used to be mounted around one of the user's limbs to hold the covering frame on the user's limb.

In use, the covering frames of the conventional adjustable limb protective assembly can be respectively moved relative to the extending arms of the main body to adjust the positions of the covering frames relative to the jointing connector of the main body to fit with the different users' limbs. However, after a total length of the conventional adjustable limb protective assembly has been set for use on the user's limb, the total length of the conventional adjustable limb protective assembly may be unexpectedly changed by unintentional pressing on the pressing buttons of the connecting bases that makes the covering frames move relative to the extending arms. Then, the changed length of the conventional adjustable limb protective assembly will change the positions of the covering frames and cannot provide a stable protective effect to the user's injured limb, and this is unsafe in use.

To overcome the shortcomings, the present invention tends to provide an adjustable limb protective assembly to mitigate the aforementioned problems.

SUMMARY OF THE INVENTION

The main objective of the present invention is to provide an adjustable limb protective assembly that can be adjusted to fit with different users' limbs conveniently and safely.

The adjustable limb protective assembly in accordance with the present invention has a main body, a first covering frame and a second covering frame. The main body has a first extending arm, a second extending arm, two holding bases, two operating elements and a jointing connector. Each extending arm has a connecting board. The holding bases are respectively connected to the extending arms adjacent the connecting boards. The operating elements are respectively and securely mounted on the connecting boards, and each one of the operating elements has an operating mount and an operating stem. The jointing connector is connected to the extending arms. The first covering frame is connected to the first extending arm and has a first supporting arm and a first covering base. The second covering frame is connected to the second extending arm and has a second supporting arm and a second covering base.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
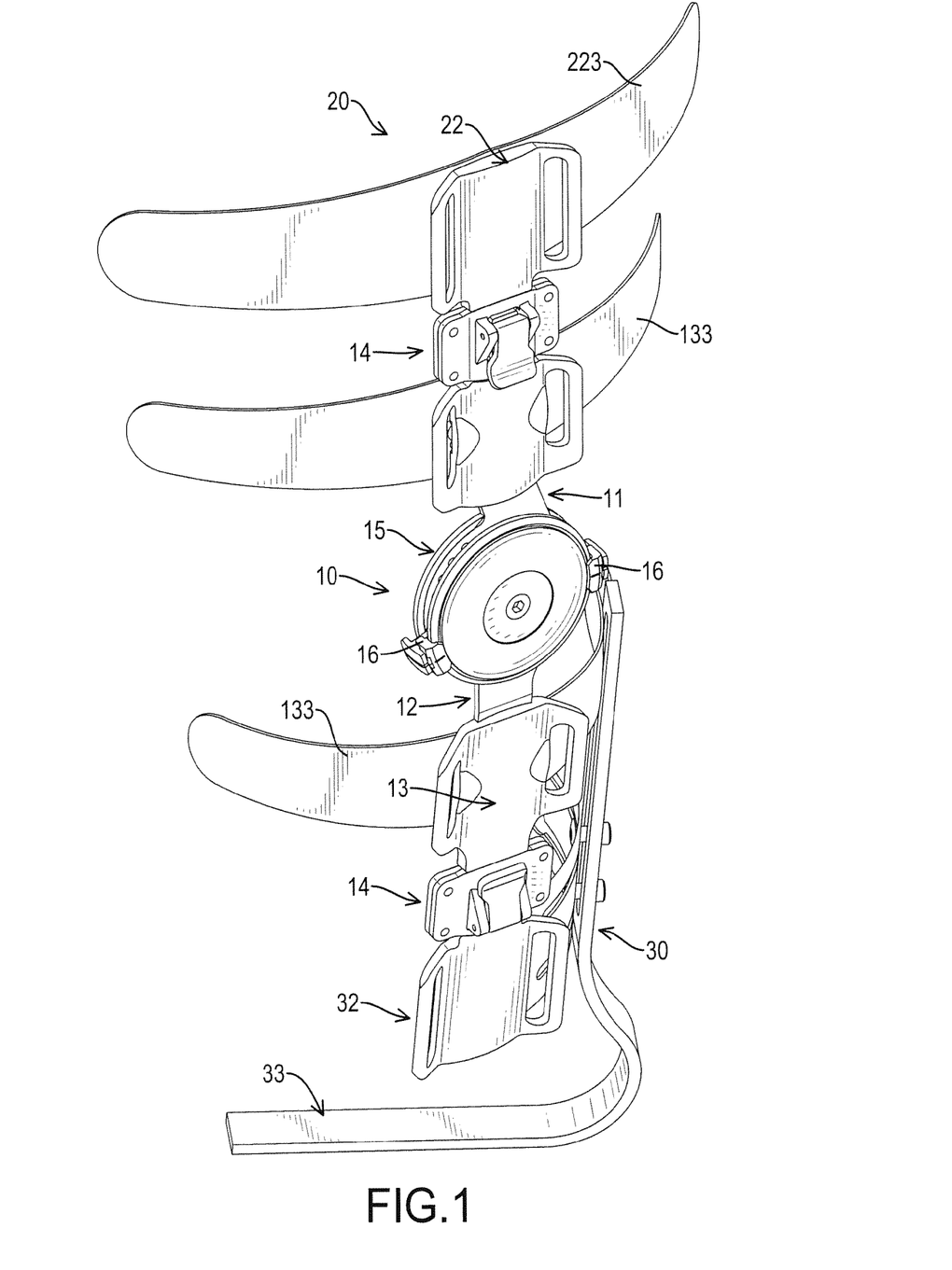
FIG. 1 is a perspective view of an adjustable limb protective assembly in accordance with the present invention.
Figure 2:
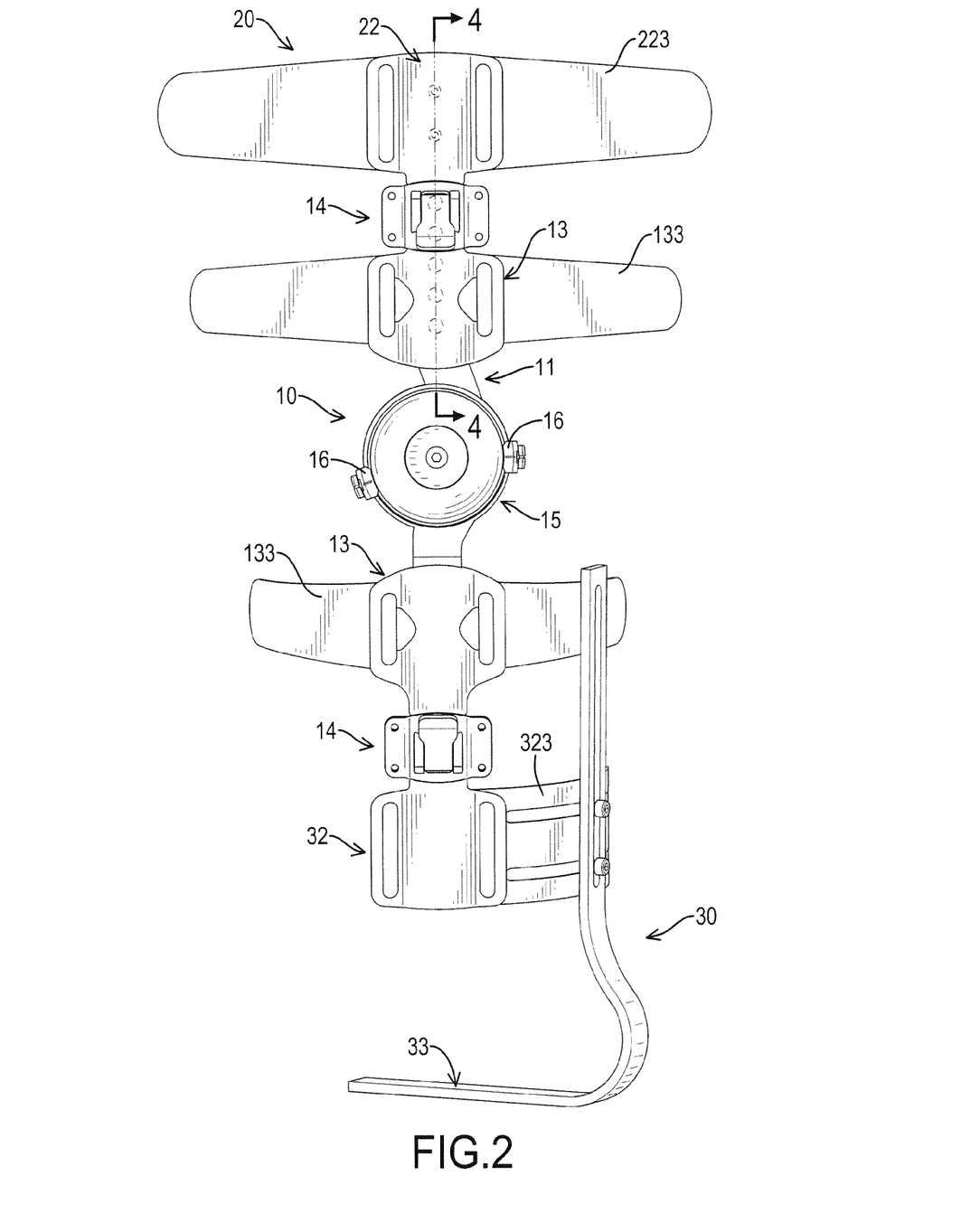
FIG. 2 is side view of the adjustable limb protective assembly in FIG. 1.

With reference to FIGS. 1 and 2, an adjustable limb protective assembly in accordance with the present invention comprises a main body 10, a first covering frame 20 and a second covering frame 30.

The main body 10 has a first extending arm 11, a second extending arm 12, two holding bases 13, two operating elements 14, a jointing connector 15 and two anti-pressing blocks 16.

Figure 5:
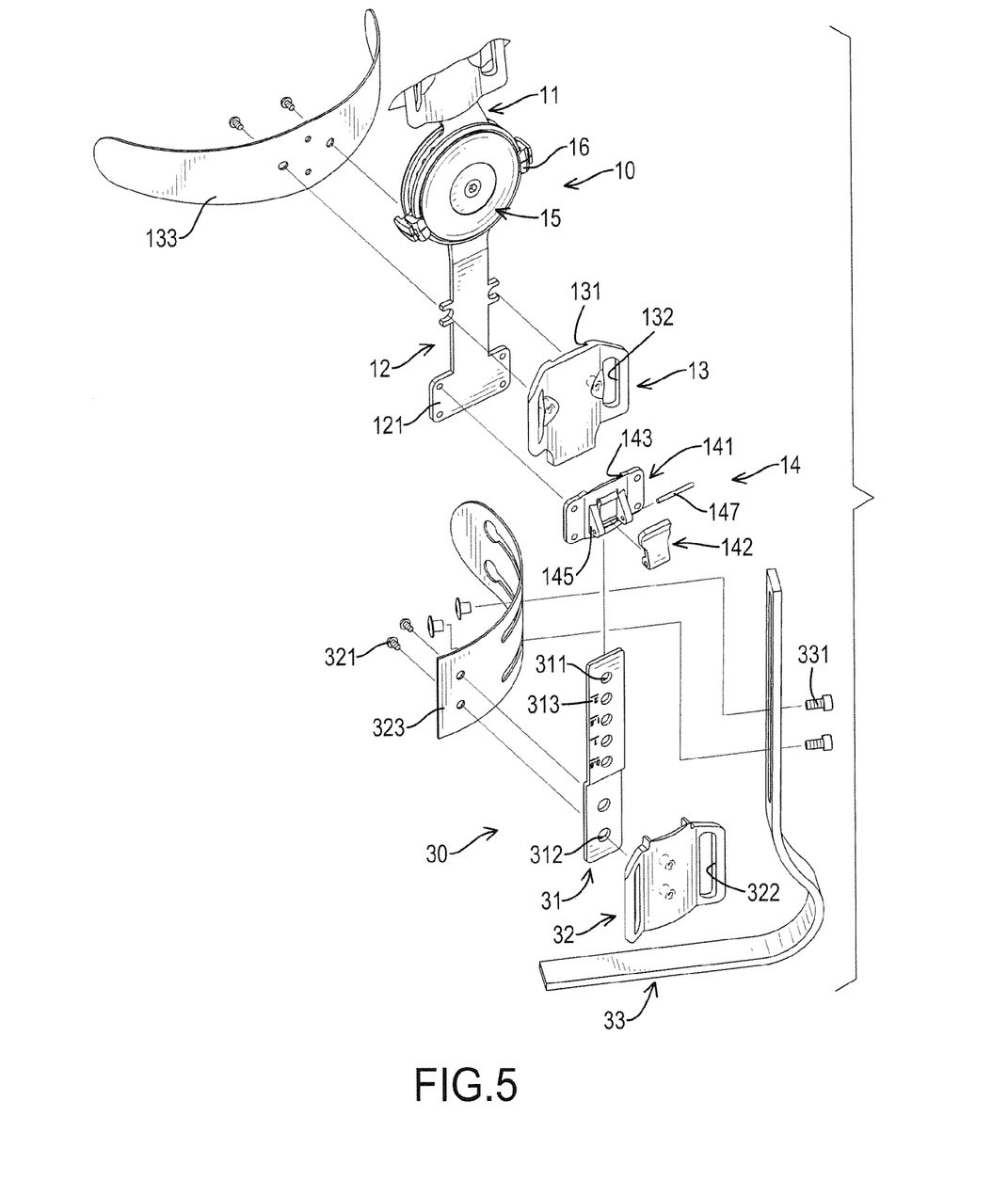
FIG. 5 is another enlarged and exploded perspective view of the adjustable limb protective assembly in FIG. 1.

The first extending arm 11 has a pivot end, a connecting end, an outer face, an inner face, and a connecting board 111. The connecting board 111 may be rectangular and is formed on and protrudes from the connecting end of the first extending arm 11. With reference to FIG. 5, the second extending arm 12 is pivotally connected to the first extending arm 11 and has a pivot end, a connecting end, an outer face, an inner face and a connecting board 121. The pivot end of the second extending arm 12 is pivotally connected to the pivot end of the first extending arm 11. The connecting board 121 of the second extending arm is formed on and protrudes from the connecting end of the second extending arm 12.

Figures 3A, 3B:
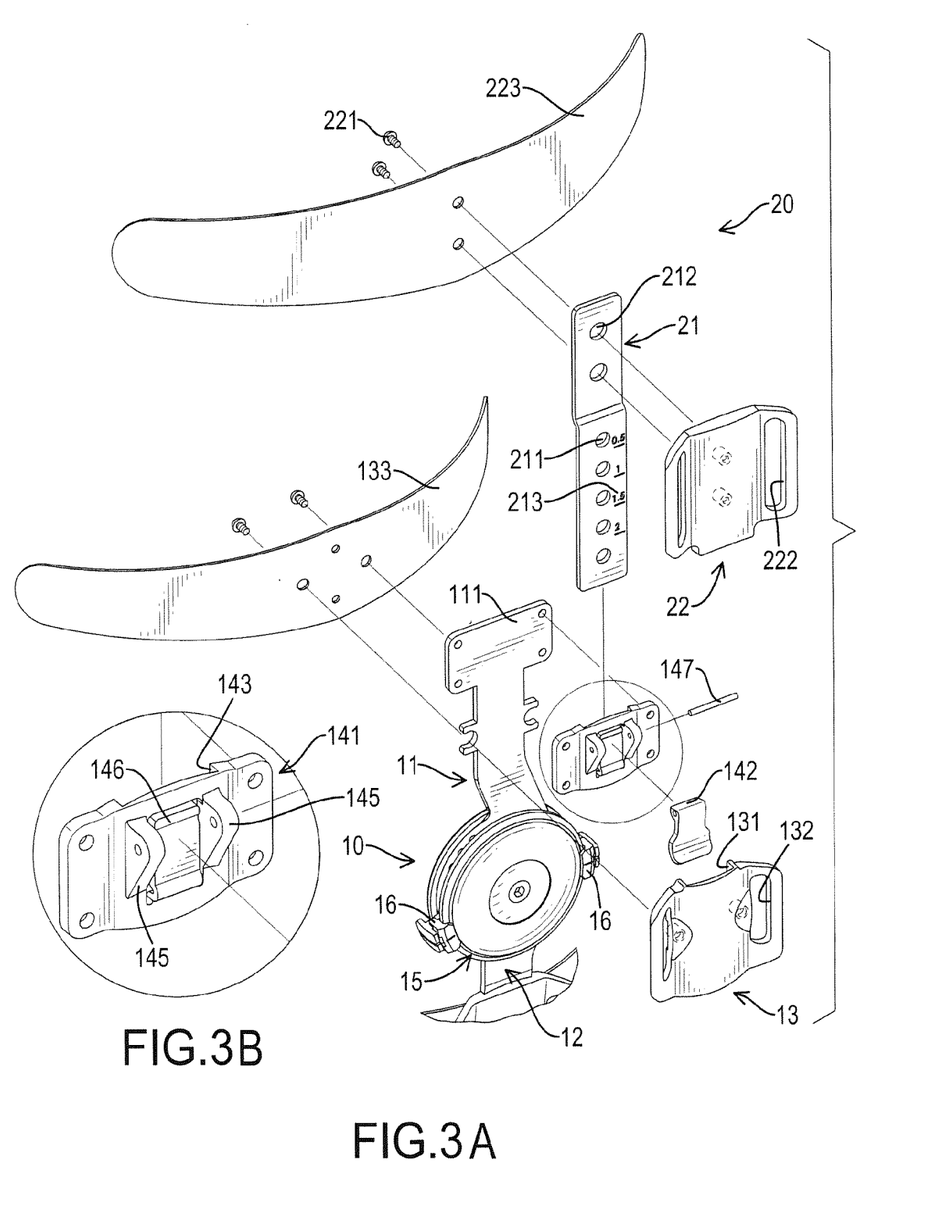
FIG. 3A is an enlarged and exploded perspective view of the adjustable limb protective assembly in FIG. 1.
FIG. 3B is an elongated perspective view of an operating element the adjustable limb protective assembly in FIG. 3A.
Figure 4:
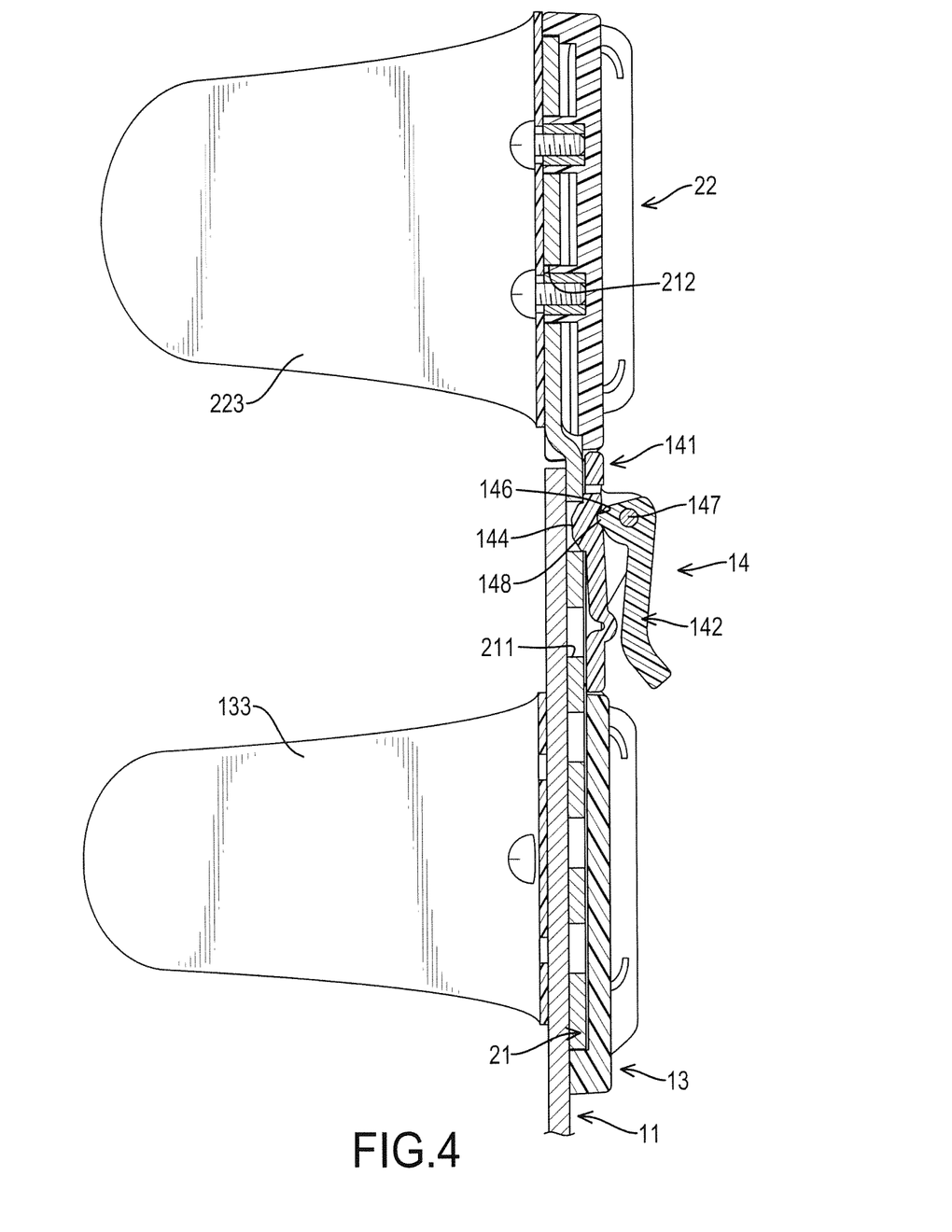
FIG. 4 is an enlarged cross sectional side view of the adjustable limb protective assembly along line 4-4 in FIG. 2.

With reference to FIGS. 3A, 4 and 5, the holding bases 13 are respectively connected to the extending arms 11, 12 adjacent the connecting boards 111, 121, and each one of the holding bases 13 has an inner face, atop side, two opposite sidewalls, a holding recess 131, two belt holes 132 and a covering pad 133. The inner faces of the holding bases 13 respectively face the outer faces of the extending arms 11, 12. The holding recess 131 is formed in the inner face of the holding base 13 and is formed through the top side of the holding base 13. The belt holes 132 are respectively formed through the opposite sidewalls of the holding base 13 beside the holding recess 131. The covering pad 133 abuts the inner face of a corresponding extending arm 11, 12 and is connected to the inner face of the holding base 13.

With reference to FIGS. 3A and 3B, the operating elements 14 are respectively and securely mounted on the connecting boards 111, 121, and each one of the operating elements 14 has an operating mount 141 and an operating stem 142. The operating mount 141 is securely mounted on the connecting board 111, 121 of a corresponding extending arm 11, 12 at the outer face of the extending arm 11, 12 and has an inner face, an outer face, a connecting recess 143, an engaging protrusion 144, two protruding wings 145 and a positioning slot 146.

The inner face of the operating mount 141 abuts the corresponding connecting board 111, 121. The connecting recess 143 is formed in the inner face of the operating mount 141, communicates with the holding recess 131 of the holding base 13 that is connected to the corresponding extending arm 11, 12, and has a bottom face. With reference to FIG. 4, the engaging protrusion 144 may be circular and is formed on and protrudes from the bottom face of the connecting recess 143. The protruding wings 145 are formed on and protrude from the outer face of the operating mount 141 and are parallel with each other at an interval. The positioning slot 146 is formed in the outer face of the operating mount 141 between the protruding wings 145 at a position corresponding to the engaging protrusion 144.

The operating stem 142 is pivotally connected to the operating mount 141 at the outer face of the operating mount 141 and has an inner face, a pivotal end, a toggle end, a pivot rod 147 and a pushing tab 148. The inner face of the operating stem 142 faces the outer face of the operating mount 141. The pivotal end of the operating stem 142 is mounted between the protruding wings 145. The toggle end of the operating stem 142 is curved and extends out of the protruding wings 145. The pivot rod 147 is mounted through the pivotal end of the operating stem 142 and is connected to the protruding wings 145 to enable the operating stem 142 to rotate relative to the operating mount 141. The pushing tab 148 is formed on and protrudes from the inner face of the operating stem 142 at the pivotal end of the operating stem 142 and is selectively mounted in the positioning slot 146 when the operating stem 142 is rotated relative to the operating mount 141.

Figure 6:
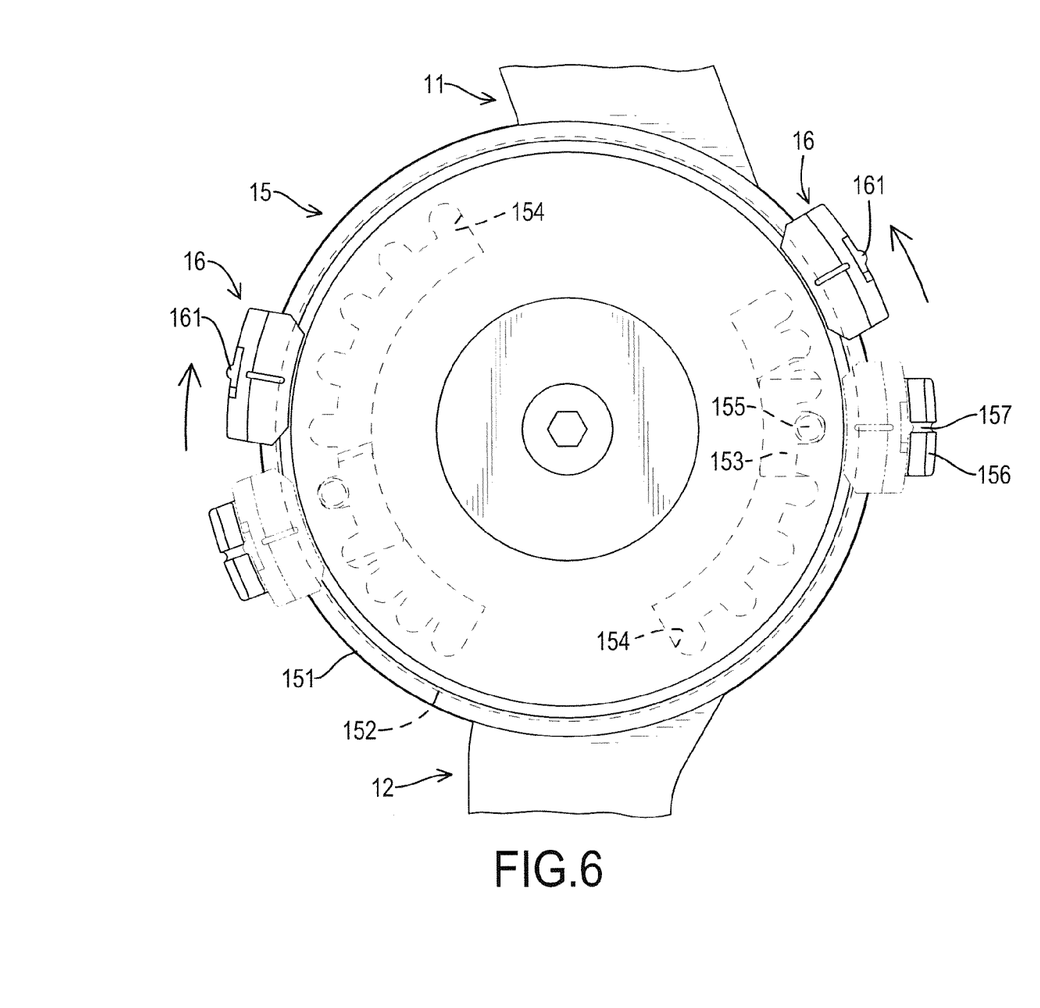
FIG. 6 is an enlarged and operational side view of the adjustable limb protective assembly in FIG. 1 for adjusting an angle of the adjustable limb protective assembly.

With reference to FIGS. 1 and 6, the jointing connector 15 is connected to the pivot ends of the extending arms 11, 12 and has two limiting covers 151, an engaging disk 152 and two limiting buttons 153. The limiting covers 151 are connected to the extending arms 11, 12 to cover the pivot ends of the extending arms 11, 12 and are parallel with each other by a gap. The engaging disk 152 is mounted between the limiting covers 151, abuts the pivot end of one of the extending arms 11, 12, and has two limiting slots 154. The limiting slots 154 are formed through the engaging disk 152, and each one of the limiting slots 154 has multiple positioning segments formed in the limiting slot 154 at intervals.

The limiting buttons 153 are movably mounted between the limiting covers 151, selectively engage the engaging disk 152, and each one of the limiting buttons 153 has an inner end, an outer end, an engaging rod 155 and a switching tab 156. The inner end of the limiting button 153 extends into the jointing connector 15 between the engaging disk 152 and the pivot end of one of the extending arms 11, 12. The outer end of the limiting button 153 extends out of the limiting covers 151. The engaging rod 155 is connected to the inner end of the limiting button 153 and engages between two adjacent positioning segments of one of the limiting slots 154 of the engaging disk 152 to limit an angle between the extending arms 11, 12. The switching tab 156 is formed on and protrudes from the outer end of the limiting button 153, axially extends above the limiting covers 151, and has an external surface and a locating recess 157 formed on the external surface of the switching tab 156. In addition, the jointing connector 15 is conventional and the features and the structures of the jointing connector 15 are not described in detail.

The anti-pressing blocks 16 are slidably mounted on one of the limiting covers 151, respectively engage the switching tabs 156 of the limiting buttons 153 to prevent the limiting buttons 153 from moving relative to the engaging disk 152, and this can prevent the angle between the extending arms 11, 12 from being changed after setting. Each one of the anti-pressing blocks 16 has an inner side, an outer side and a positioning point 161. The inner side of the anti-pressing block 16 is slidably mounted around the corresponding limiting cover 151. The outer side of the anti-pressing block 16 selectively abuts the switching tab 156 of the corresponding limiting button 153. The positioning point 161 is formed on and protrudes from the outer side of the anti-pressing block 16 and selectively engages in the locating recess 157 of the corresponding switching tab 156.

With reference to FIGS. 3A and 4, the first covering frame 20 is connected to the first extending arm 11 of the main body 10 and has a first supporting arm 21 and a first covering base 22.

The first supporting arm 21 movably abuts the first extending arm 11, is connected to the holding base 13 and the operating element 14 that are connected to the first extending arm 11, and has an inner face, an outer face, an inserting end, an extending end, multiple engaging holes 211, at least one connecting hole 212 and a graduated scale 213. The inner face of the first supporting arm 21 abuts the outer face of the first extending arm 11 and the connecting board 111 of the first extending arm 11. The inserting end of the first supporting arm 21 is mounted in the holding recess 131 of the corresponding holding base 13 via the connecting recess 143 of the corresponding operating mount 141. The extending end of the first supporting arm 21 extends out of the connecting board 111 of the first extending arm 11 and the corresponding holding base 13.

The engaging holes 211 are formed through the inner face and the outer face of the first supporting arm 21 at intervals, and one of the engaging holes 211 engages the engaging protrusion 144 of the corresponding operating mount 141 when the pushing tab 148 of the corresponding operating stem 142 is mounted in the positioning slot 146 of the corresponding operating mount 141. The engagement between the engaging protrusion 144 and the corresponding engaging hole 211 can hold the first supporting arm 21 securely with the first extending arm 11. In addition, by engaging the engaging protrusion 144 of the corresponding operating mount 141 in different engaging holes 211 of the first supporting arm 21, a distance between the extending end of the first supporting arm 21 and the connecting board 111 of the first extending arm 11 can be changed.

The at least one connecting hole 212 is formed through the inner face and the outer face of the first supporting arm 21 adjacent the extending end of the first supporting arm 21. The graduated scale 213 is mounted on the outer face of the first supporting arm 21 adjacent the engaging holes 211.

The first covering base 22 is securely connected to the extending end of the first supporting arm 21 and has an inner side, two opposite sidewalls, at least one fastener 221, two belt holes 222 and a covering pad 223. The inner side of the first covering base 22 faces the outer face of the first supporting arm 21 adjacent the extending end of the first supporting arm 21. The at least one fastener 221 is mounted through the at least one connecting hole 212 of the first supporting arm 21 and is connected securely to the inner side of the first covering base 22 to hold the first covering base 22 securely with the first supporting arm 21. The belt holes 222 are respectively formed through the opposite sidewalls of the first covering base 22. The covering pad 223 is connected to the inner face of the first supporting arm 21 adjacent the extending end of the first supporting arm 21 by the at least one fastener 221 mounted through the covering pad 223 of the first covering base 22.

With reference to FIG. 5, the second covering frame 30 is connected to the second extending arm 12 of the main body 10 and has a second supporting arm 31, a second covering base 32 and a gripping arm 33.

The second supporting arm 31 movably abuts the second extending arm 12, is connected to the holding base 13 and the operating element 14 that are connected to the second extending arm 12, and has an inner face, an outer face, an inserting end, an extending end, multiple engaging holes 311, at least one connecting hole 312 and a graduated scale 313. The inner face of the second supporting arm 31 abuts the outer face of the second extending arm 12 and the connecting board 121 of the second extending arm 12. The inserting end of the second supporting arm 31 is mounted in the holding recess 131 of the corresponding holding base 13 via the connecting recess 143 of the corresponding operating mount 141. The extending end of the second supporting arm 21 extends out of the connecting board 121 of the second extending arm 12 and the corresponding holding base 13.

The engaging holes 311 are formed through the inner face and the outer face of the second supporting arm 21 at intervals, and one of the engaging holes 311 engages the engaging protrusion 144 of the corresponding operating mount 141 when the pushing tab 148 of the corresponding operating stem 142 is mounted in the positioning slot 146 of the corresponding operating mount 141. The engagement between the engaging protrusion 144 and the corresponding engaging hole 311 of the second supporting arm 31 can hold the second supporting arm 31 securely with the second extending arm 12. Furthermore, by engaging the engaging protrusion 144 of the corresponding operating mount 141 in different engaging holes 311 of the second supporting arm 31, a distance between the extending end of the second supporting arm 31 and the connecting board 121 of the second extending arm 12 can be changed.

The at least one connecting hole 312 is formed through the inner face and the outer face of the second supporting arm 31 adjacent the extending end of the second supporting arm 31. The graduated scale 313 is mounted on the outer face of the second supporting arm 31 adjacent the engaging holes 311 of the second supporting arm 31.

The second covering base 32 is securely connected to the extending end of the second supporting arm 31 and has an inner side, two opposite sidewalls, at least one fastener 321, two belt holes 322 and a covering pad 323. The inner side of the second covering base 32 faces the outer face of the second supporting arm 31 adjacent the extending end of the second supporting arm 31. The at least one fastener 321 is mounted through the at least one connecting hole 312 of the second supporting arm 31 and is connected securely to the inner side of the second covering base 32 to hold the second covering base 32 securely with the second supporting arm 31. The belt holes 322 are respectively formed through the opposite sidewalls of the second covering base 32. The covering pad 323 is connected to the inner face of the second supporting arm 31 adjacent the extending end of the second supporting arm 31 by the at least one fastener 321 mounted through the covering pad 323 of the second covering base 32.

The gripping arm 33 may be L-shaped, is connected to the covering pad 323 of the second covering base 32 by multiple bolts 331 mounted through the gripping arm 33 and the covering pad 323 of the second covering base 32.

Figure 7:
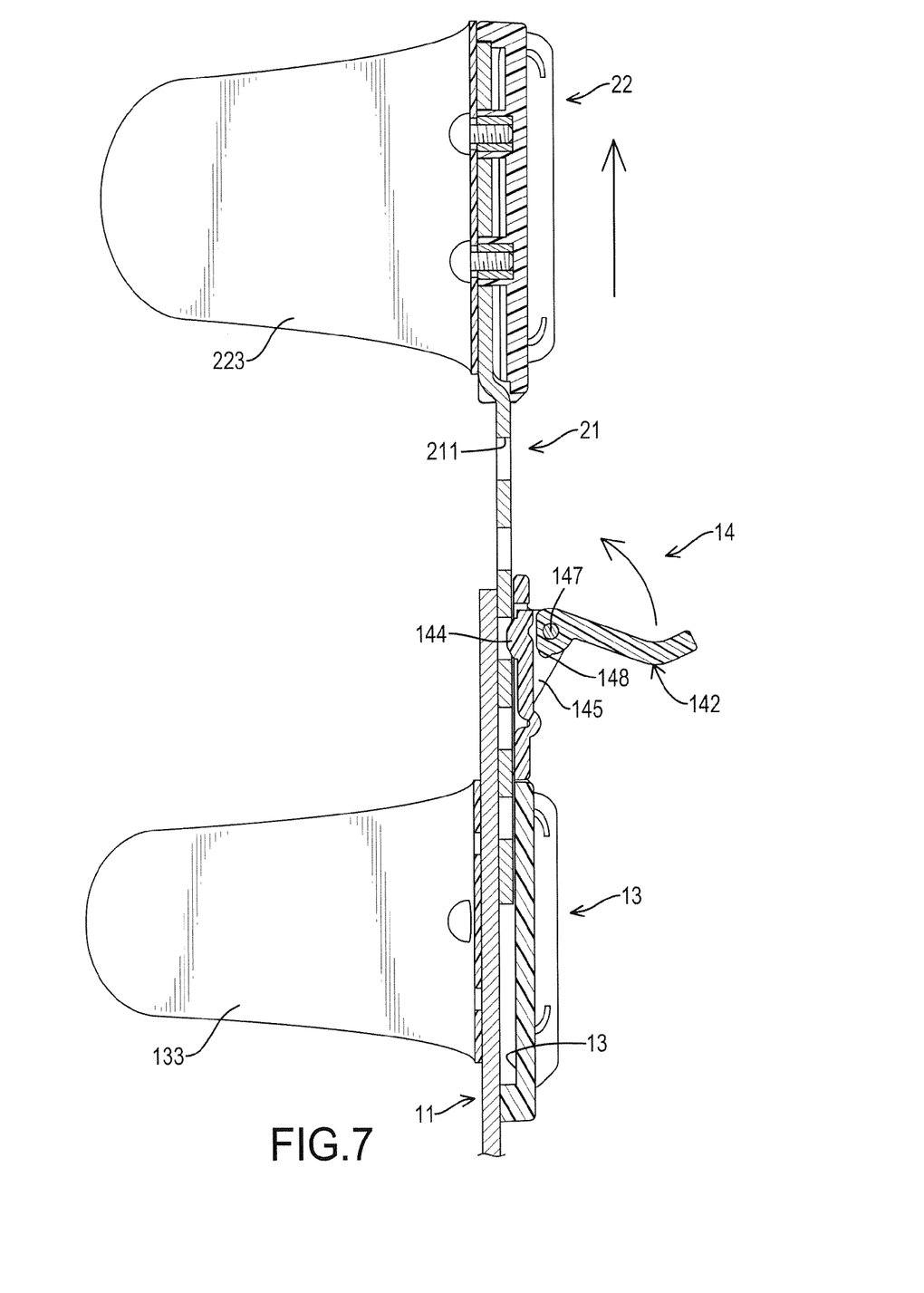
FIG. 7 is an enlarged and operational side view of the adjustable limb protective assembly in FIG. 1 for changing a length of the adjustable limb protective assembly.

With reference to FIG. 7, when the adjustable limb protective assembly is mounted on an arm of a user, the positions of the supporting arms 21, 31 can be adjusted according to a length of the user's arm by switching the toggle ends of the operating stems 142 to rotate relative to the operating mounts 141 to enable the pushing tabs 148 to disengage from the positioning slots 146. Then, the user can push the supporting arms 21, 31 to move relative to the holding bases 13 and the operating elements 14, and this can enable the engaging protrusions 144 to deform and to respectively disengage from the corresponding engaging holes 211, 311 of the supporting arms 21, 31. After moving the supporting arms 21, 31 relative to the extending arms 11, 12 to adjust the total length of the adjustable limb protective assembly to fit with the user's arm, the user can switch the operating stems 142 to rotate back to the original positions to push the corresponding engaging protrusions 144 via the pushing tabs 148 and the positioning slots 146 to respectively engage other engaging holes 211, 311 of the supporting arms 21, 31. Then, the supporting arms 21, 31 can be securely and respectively held with the extending arms 11, 21 by the engagement between the engaging protrusions 144 and the corresponding engaging holes 211, 311 of the supporting arms 21, 31.

Figure 8:
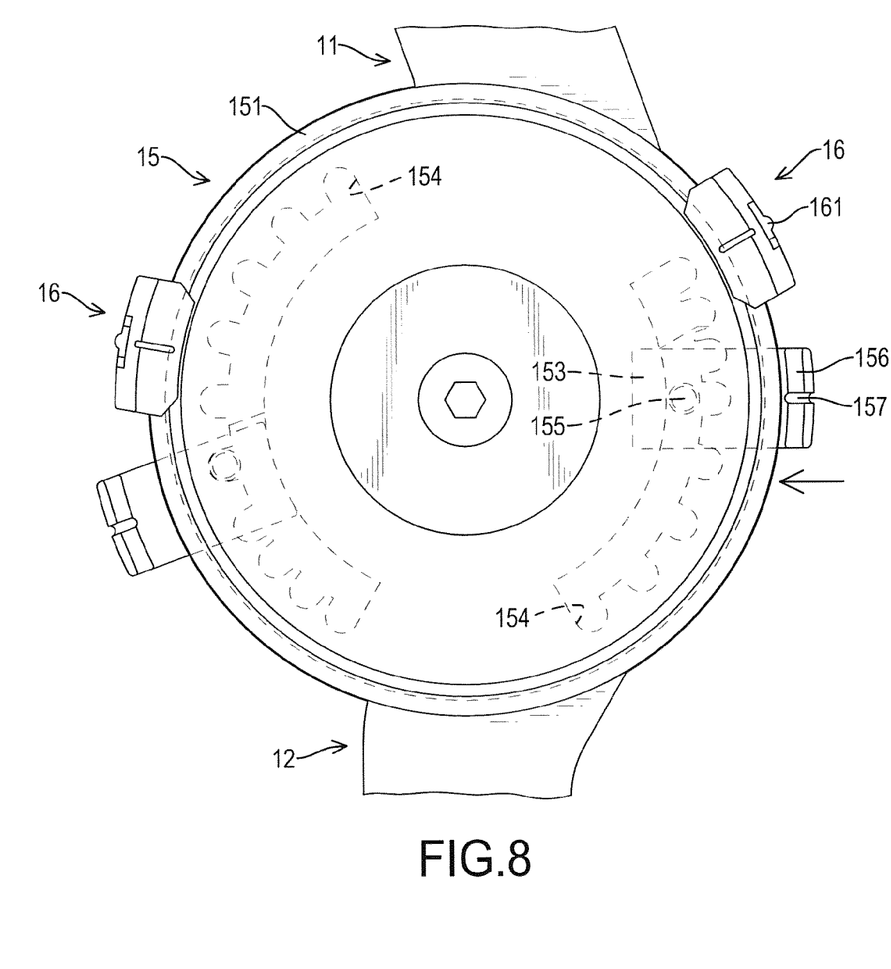
FIG. 8 is another enlarged and operational side view of the adjustable limb protective assembly in FIG. 1 for adjusting an angle of the adjustable limb protective assembly.

In addition, with reference to FIG. 8, the user also can adjust an angle between the extending arms 11, 12 by moving the anti-pressing blocks 16 along the corresponding limiting cover 151 to disengage from the limiting buttons 153. Then, the limiting buttons 153 can be moved inwardly relative to the engaging disk 152 by pushing the switching tabs 156 and this can enable the engaging rods 155 to disengage from the two corresponding adjacent positioning segments of the limiting slots 154 of the engaging disk 152. With the disengagement between the engaging rods 155 of the limiting buttons 153 and the limiting slots 154 of the engaging disk 152, the extending arms 11, 12 can be rotated relative to the jointing connector 15 to adjust an angle between the covering frames 20, 30 to fit with an angle of the user's arm.

After adjusting the angle between the covering frames 20, 30 to fit with the angle of the user's arm, the anti-pressing blocks 16 are moved backwardly to the original positions to enable the positioning points 161 to respectively engage the locating recesses 157 of the switching tabs 156. Then, the limiting buttons 153 cannot be moved relative to the engaging disk 152 and the angle between the extending arms 11, 12 can be held securely to ensure that the angle between the covering frames 20, 30 will not be changed.

Figure 9:
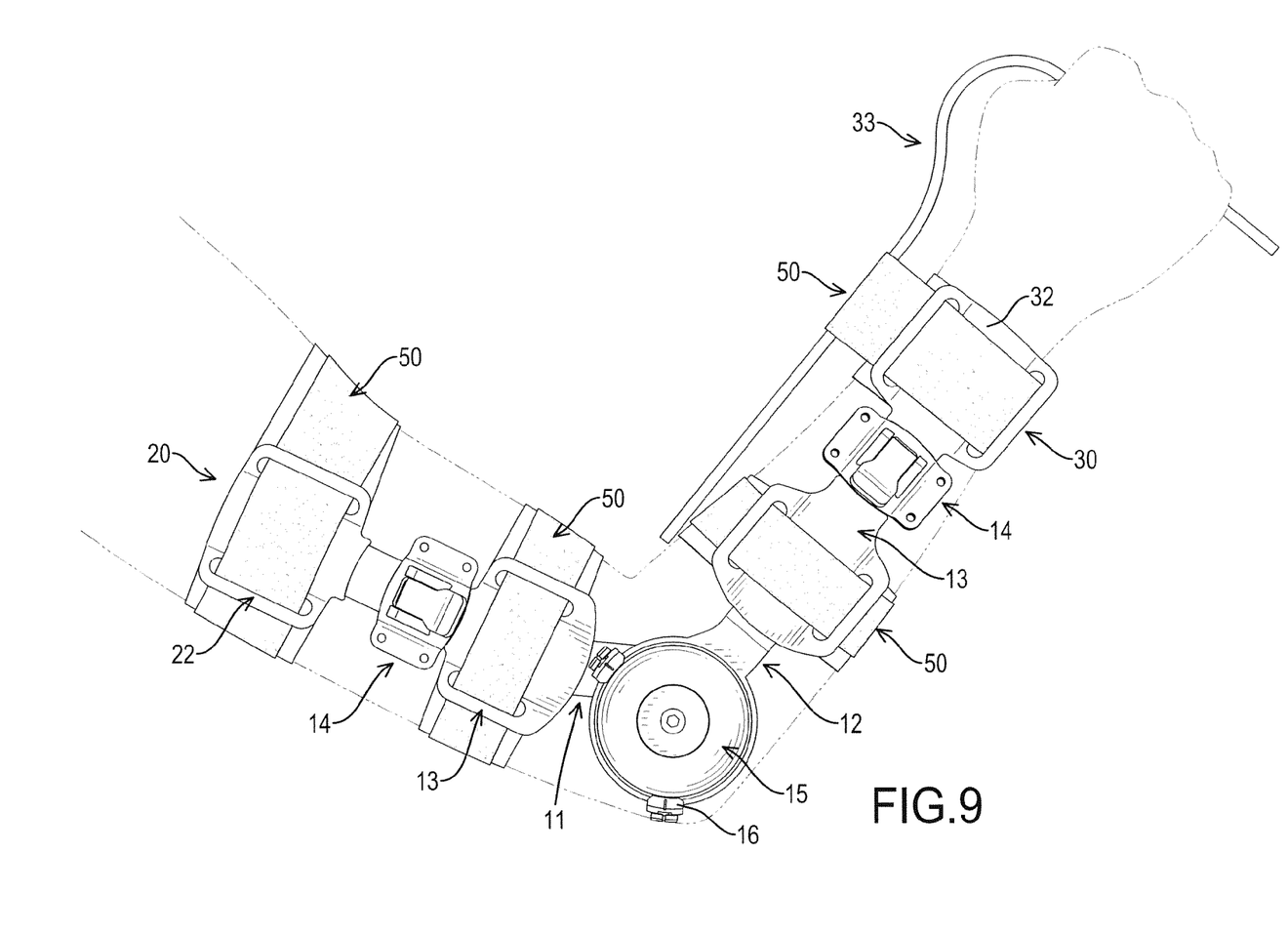
FIG. 9 is an operational side view of the adjustable limb protective assembly in FIG. 1, mounted on a user's arm.

Furthermore, with reference to FIG. 9, after adjusting the length and the angle of the adjustable limb protective assembly, the covering pads 133, 223, 323 are mounted on the user's arm, and multiple belts 50 are connected to the belt holes 132, 222, 322 of the holding bases 13 and the covering bases 22, 32 to be mounted around the user's arm, and this can securely and conveniently hold the adjustable limb protective assembly with the user's arm to make the arm of the user positioned between the covering frames 20, 30 for effective protection. Additionally, the gripping arm 33 facilitates ease of holding for the user's hand.

According to the above-mentioned features and structural relationships of the adjustable limb protective assembly in accordance with the present invention, the operating stems 142 of the operating elements 14 are securely held with the operating mounts 141 by the engagement between the pushing tabs 148 and the positioning slots 146. Then, when a user unintentionally presses or abuts against the operating stems 142, the operating stems 142 will not easily rotate relative to the operating mounts 141 and this can prevent the supporting arms 21, 31 from moving relative to the extending arms 11. 12. Consequently, the total length of the adjustable limb protective assembly can be securely held to provide a stable protective effect to the user's injured limbs and this is safe in use.

In addition, the engagement between the anti-pressing blocks 16 and the limiting buttons 153 of the jointing connector 15 can prevent the limiting buttons 153 from moving relative to the engaging disk 152 via pressing the switching tabs 156, and this can ensure that the angle between the extending arms 11, 12 stay fixed after adjustment and this also can provide a stable protective effect to the user's injured limbs safely.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An adjustable limb protective assembly having:
    a main body having
        a first extending arm having
            a pivot end;
            a connecting end;
            an outer face;
            an inner face; and
            a connecting board formed on and protruding from the connecting end of the first extending arm;
        a second extending arm pivotally connected to the first extending arm and having
            a pivot end pivotally connected to the pivot end of the first extending arm;
            a connecting end;
            an outer face;
            an inner face; and
            a connecting board formed on and protruding from the connecting end of the second extending arm;
        two holding bases respectively connected to the extending arms adjacent the connecting boards, and each one of the holding bases having
            an inner face facing the outer face of a corresponding extending arm;
            a top side;
            two opposite sidewalls; and
            a holding recess formed in the inner face of the holding base and formed through the top side of the holding base;
        two operating elements respectively and securely mounted on the connecting boards, and each one of the operating elements having
            an operating mount securely mounted on the connecting board of a corresponding extending arm at the outer face of the corresponding extending arm and having
                an inner face abutting the connecting board of the corresponding extending arm;
                an outer face;
                a connecting recess formed in the inner face of the operating mount, communicating with the holding recess of the holding base that is connected to the corresponding extending arm and having a bottom face;
                an engaging protrusion formed on and protruding from the bottom face of the connecting recess;
                two protruding wings formed on and protruding from the outer face of the operating mount and parallel with each other at an interval; and
                a positioning slot formed in the outer face of the operating mount between the protruding wings at a position corresponding to the engaging protrusion; and
            an operating stem pivotally connected to the operating mount at the outer face of the operating mount and having
                an inner face facing the outer face of the operating mount;
                a pivotal end mounted between the protruding wings;
                a toggle end extending out of the protruding wings;
                a pivot rod mounted through the pivotal end of the operating stem and connected to the protruding wings to enable the operating stem to rotate relative to the operating mount; and
                a pushing tab formed on and protruding from the inner face of the operating stem at the pivotal end of the operating stem and selectively mounted in the positioning slot when the operating stem is rotated relative to the operating mount; and
        a jointing connector connected to the pivot ends of the extending arms;
    a first covering frame connected to the first extending arm of the main body and having
        a first supporting arm movably abutting the first extending arm, connected to the holding base and the operating element that are connected to the first extending arm, and having
            an inner face abutting the outer face of the first extending arm and the connecting board of the first extending arm;
            an outer face;

an inserting end mounted in the holding recess of the corresponding holding base via the connecting recess of the corresponding operating mount;

an extending end extending out of the connecting board of the first extending arm and the corresponding holding base; and multiple engaging holes formed through the inner face and the outer face of the first supporting arm at intervals, and one of the engaging holes engaging the engaging protrusion of the corresponding operating mount when the pushing tab of the corresponding operating stem is mounted in the positioning slot of the corresponding operating mount; and a first covering base securely connected to the extending end of the first supporting arm; and a second covering frame connected to the second extending arm of the main body and having a second supporting arm movably abutting the second extending arm, connected to the holding base and the operating element that are connected to the second extending arm, and having an inner face abutting the outer face of the second extending arm and the connecting board of the second extending aim;

an outer face;

an inserting end mounted in the holding recess of the corresponding holding base via the connecting recess of the corresponding operating mount;

an extending end extending out of the connecting board of the second extending arm and the corresponding holding base; and multiple engaging holes formed through the inner face and the outer face of the second supporting arm at intervals, and one of the engaging holes engaging the engaging protrusion of the corresponding operating mount when the pushing tab of the corresponding operating stem is mounted in the positioning slot of the corresponding operating mount; and a second covering base securely connected to the extending end of the second supporting arm.

2. The adjustable limb protective assembly as claimed in claim 1, wherein the jointing connector has two limiting covers connected to the extending arms to cover the pivot ends of the extending arms and parallel with each other by a gap;

an engaging disk mounted between the limiting covers, abutting the pivot end of one of the extending arms, and having two limiting slots formed through the engaging disk, and each one of the limiting slots having multiple positioning segments formed in the limiting slot at intervals; and two limiting buttons movably mounted between the limiting covers, selectively engaging the engaging disk, and each one of the limiting buttons having an inner end extending into the jointing connector between the engaging disk and the pivot end of one of the extending arms;

an outer end extending out of the limiting covers;

an engaging rod connected to the inner end of the limiting button and engaging between two adjacent positioning segments of one of the limiting slots of the engaging disk to limit an angle between the extending arms; and a switching tab formed on and protruding from the outer end of the limiting button and axially extending above the limiting covers; and the main body has two anti-pressing blocks slidably mounted on one of the limiting covers, respectively engaging the switching tabs of the limiting buttons to prevent the limiting buttons from moving relative to the engaging disk, and each one of the anti-pressing blocks has an inner side slidably mounted around the corresponding limiting cover; and an outer side selectively abutting the switching tab of a corresponding limiting button.

3. The adjustable limb protective assembly as claimed in claim 2, wherein each one of the limiting buttons of the jointing connector has an external surface; and a locating recess formed on the external surface of the switching tab; and each one of the anti-pressing blocks has a positioning point formed on and protruding from the outer side of the anti-pressing block and selectively engaging in the locating recess of a corresponding switching tab.

4. The adjustable limb protective assembly as claimed in claim 3, wherein each one of the holding bases has two belt holes respectively formed through the opposite sidewalls of the holding base beside the holding recess; and a covering pad abutting the inner face of a corresponding extending arm and connected to the inner face of the holding base.

5. The adjustable limb protective assembly as claimed in claim 4, wherein the first supporting arm has at least one connecting hole formed through the inner face and the outer face of the first supporting arm adjacent the extending end of the first supporting arm; and the first covering base has an inner side facing the outer face of the first supporting arm adjacent the extending end of the first supporting arm;

two opposite sidewalls; and at least one fastener mounted through the at least one connecting hole of the first supporting arm and connected securely to the inner side of the first covering base to hold the first covering base securely with the first supporting arm.

6. The adjustable limb protective assembly as claimed in claim 5, wherein the first covering base has two belt holes respectively formed through the opposite sidewalls of the first covering base; and a covering pad connected to the inner face of the first supporting arm adjacent the extending end of the first supporting arm by the at least one fastener mounted through the covering pad of the first covering base.

7. The adjustable limb protective assembly as claimed in claim 6, wherein the second supporting arm has at least one connecting hole formed through the inner face and the outer face of the second supporting arm adjacent the extending end of the second supporting arm; and the second covering base has an inner side facing the outer face of the second supporting arm adjacent the extending end of the second supporting arm;

two opposite sidewalls; and at least one fastener mounted through the at least one connecting hole of the second supporting arm and connected securely to the inner side of the second covering base to hold the second covering base securely with the second supporting arm.

8. The adjustable limb protective assembly as claimed in claim 7, wherein the second covering base has
two belt holes respectively formed through the opposite sidewalls of the second covering base; and
a covering pad connected to the inner face of the second supporting arm adjacent the extending end of the second supporting arm by the at least one fastener mounted through the covering pad of the second covering base.

9. The adjustable limb protective assembly as claimed in claim 8, wherein the second covering frame has a gripping arm connected to the covering pad of the second covering base by multiple bolts mounted through the gripping arm and the covering pad of the second covering base.

10. The adjustable limb protective assembly as claimed in claim 9, wherein each one of the supporting arms has a graduated scale mounted on the outer face of the supporting arm adjacent to the engaging holes of the supporting arm.

* * * * *